US00PP24534P2

(12) United States Plant Patent
Sligh

(10) Patent No.: US PP24,534 P2
(45) Date of Patent: Jun. 10, 2014

(54) ***MICHELIA* PLANT NAMED 'FREE SPIRIT'**

(50) Latin Name: *Magnolia laevitolia*
Varietal Denomination: 'Free Spirit'

(75) Inventor: Barry E. Sligh, Lyttelton (NZ)

(73) Assignee: Plants Nouveau, Charleston, SC (US)

( * ) Notice: Subject to any disclaimer, the term of this patent is extended or adjusted under 35 U.S.C. 154(b) by 183 days.

(21) Appl. No.: 13/507,431

(22) Filed: Jun. 26, 2012

(51) Int. Cl.
*A01H 5/00* (2006.01)

(52) U.S. Cl.
USPC ..... Plt./223; Plt./226

(58) Field of Classification Search
CPC ..... A01H 5/02
USPC ..... Plt./223, 226
See application file for complete search history.

(56) References Cited

PUBLICATIONS

Pluto Upov Plant Variety Database 201304, retrieved on Feb. 6, 2014, retrieved from the Internet at <http://www.upov.int/pluto/en/index.jsp> for Magnolia 'Free Spirit' one page.*

* cited by examiner

*Primary Examiner* — June Hwu
(74) *Attorney, Agent, or Firm* — Penny J. Aguirre

(57) ABSTRACT

A new cultivar of *Magnolia laevifolia* 'Free Spirit', characterized by its very floriferous habit, its flowers that are held upright on the stems, and its low growing and broadly horizontal spreading plant habit.

2 Drawing Sheets

Botanical classification: *Magnolia laevifolia.*
Variety denomination: 'Free Spirit'.

BACKGROUND OF THE INVENTION

The present invention relates to a new and distinct cultivar of *Magnolia laevifolia* (synonym *Michelia yunnanensis*) and will be referred to hereafter by its cultivar name, 'Free Spirit'. 'Free Spirit' is a new cultivar of evergreen shrub grown for use as an ornamental landscape plant.

The Inventor discovered the new cultivar in summer of 1996 s a naturally occurring whole plant mutation in a seedbed at his nursery in Lytterton, New Zealand. The seedbed had been planted with seeds collected from an unnamed plant of *Magnolia laevifolia*. The male parent is unknown.

Asexual reproduction of the new cultivar was first accomplished under the direction of the Inventor using in vitro propagation in November of 2008 in Hastings, New Zealand. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot in Ashburton, New Zealand. These attributes in combination distinguish 'Free Spirit' as a unique cultivar of *Michelia.*

1. 'Free Spirit' exhibits a very floriferous habit.
2. 'Free Spirit' exhibits flowers that are held upright on the stems.
3. 'Free Spirit' exhibits a low growing and broadly horizontal spreading plant habit.

The probable parent plant, a typical plant of the species, *Magnolia laevifolia*, differs from 'Free Spirit' in having a bushy, upright plant habit. 'Free Spirit' can be most closely compared to the cultivars 'Velvet and Cream' (not patented) and 'MICjur01' (U.S. Plant Pat. No. 21,873) and 'Inspiration' (not patented). 'Velvet and Cream' differs from 'Free Spirit' in having an upright (tall shrub to small tree) plant habit. 'MICjur01' differs from 'Free Spirit' in having a taller plant height with a more upright plant habit and in having flowers that are light pink in color.

BRIEF DESCRIPTION OF THE DRAWING

The accompanying colored photographs illustrate the overall appearance and distinct characteristics of the new cultivar as grown outdoors in full sun in Ashburton, New Zealand.

The photograph in FIG. 1 and FIG. 2 were taken of 3-year-old plants of 'Free Spirit' as grown in 2-gallon containers. The photograph in FIG. 1 provides an overall view of 'Free Spirit' in bloom. The photograph in FIG. 2 provides an overall view of the horizontal branching of 'Free Spirit'.

Figure 1:
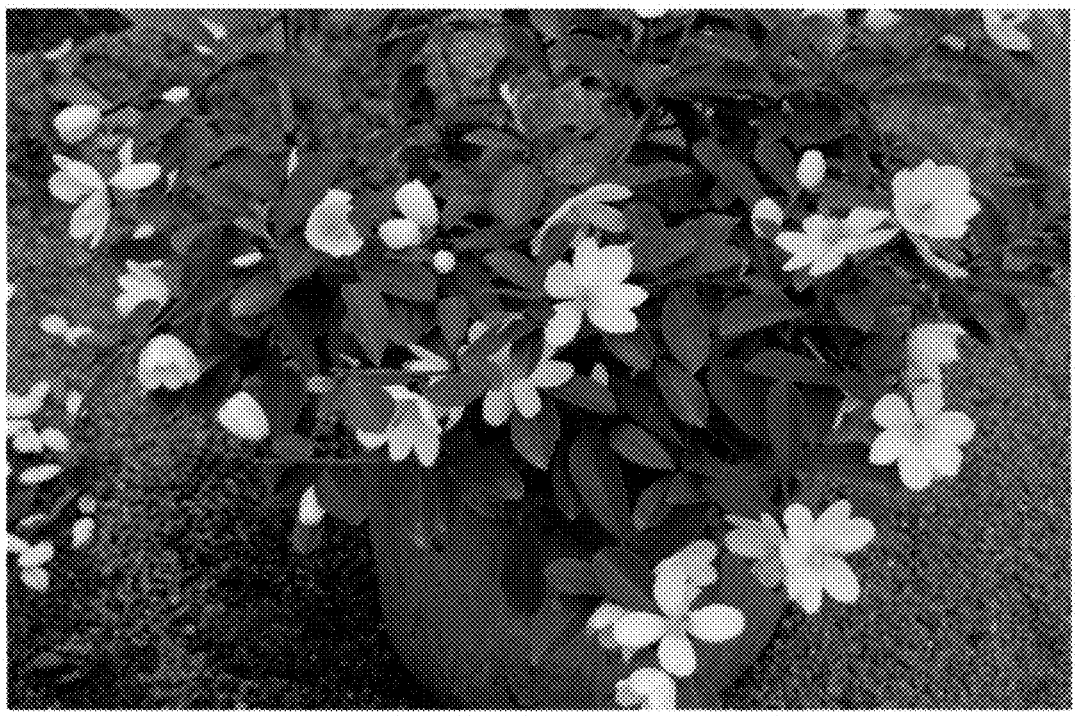
Figure 2:
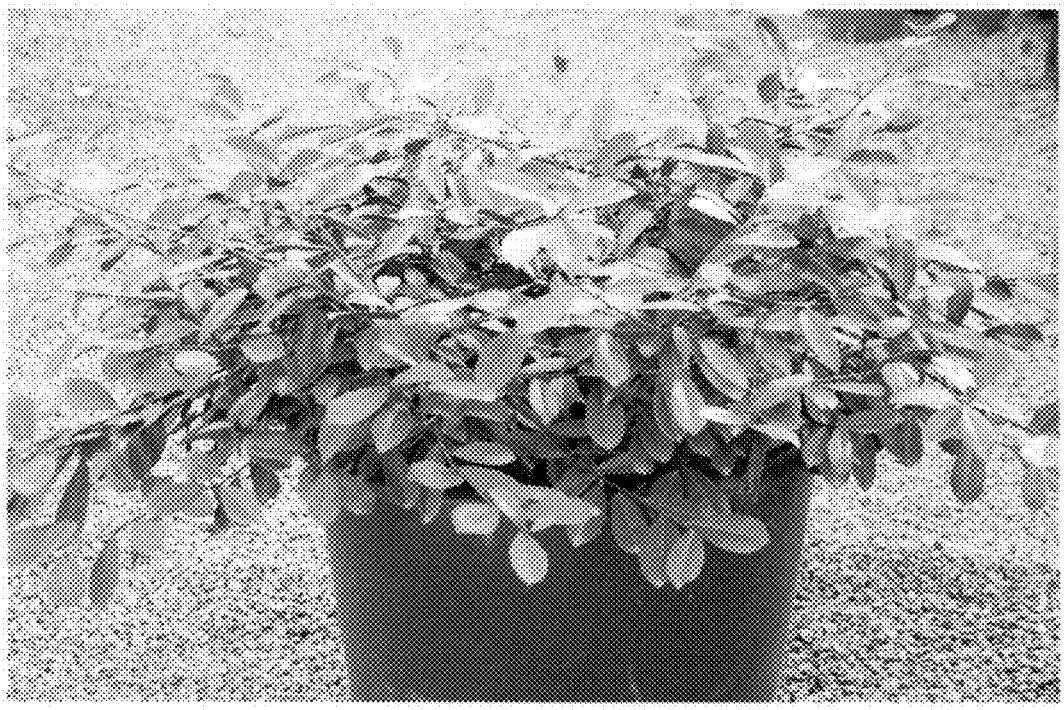
Figure 3:
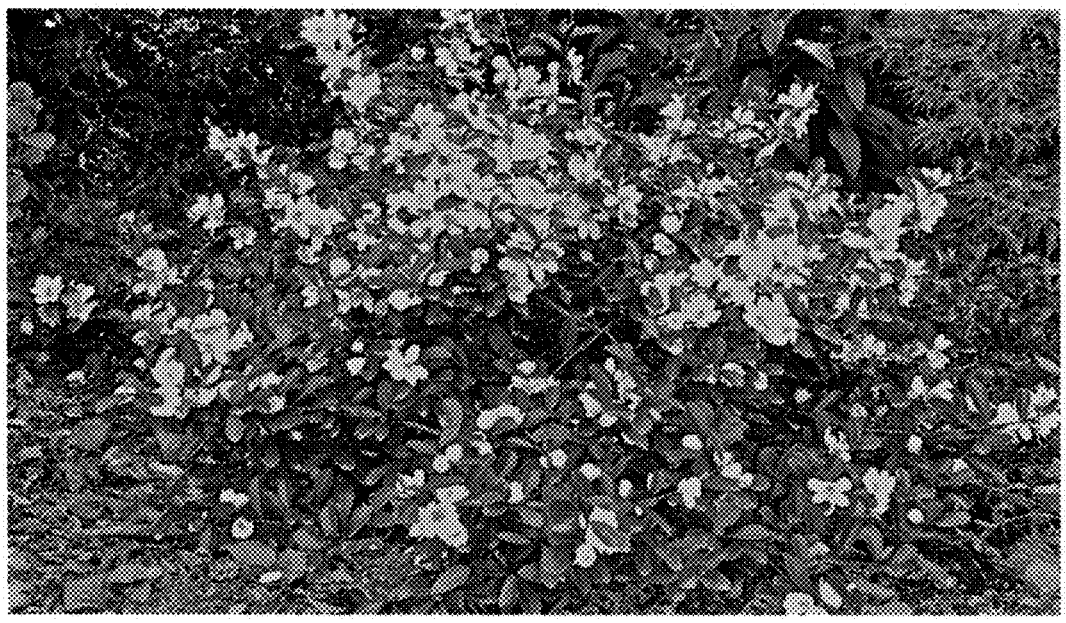

The photograph in FIG. 3 was taken of 5-year-old plant of 'Free Spirit' as grown in a garden and provides a view of the plant habit of 'Free Spirit' in the landscape.

The colors in the photograph may differ slightly from the color values cited in the detailed botanical description, which accurately describe the colors of the new *Michelia.*

DETAILED BOTANICAL DESCRIPTION

The following is a detailed description of 6 year-old plants of the new cultivar as grown outdoors in a trial garden in Ashburton, New Zealand. Plants were grown under average day temperatures of 19° C. and average night temperatures of 10° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Spring to early summer in New Zealand.

*Plant type.*—Perennial evergreen shrub.

*Plant habit.*—Low growing, broadly horizontal, spreading.

*Plant size.*—Reaches about 40 cm in height and 2.5 cm in spread.

*Hardiness.*—At least hardy in U.S.D.A. Zones 7 to 11.

*Diseases.*—Resistant, no disease problems have been observed.

*Root description.*—Main roots; dense and coarse, lateral roots; dense and fibrous.

*Environmental stress.*—Highly tolerant to wind and rain.

*Diseases and pests.*—Strong disease resistance.

*Root description.*—Main roots; dense and coarse, lateral roots; dense and fibrous, spreading and shallow, 155A in color.

*Growth rate.*—Moderate.

Stem description:

*Shape.*—Round.

*Stem color.*—New growth; between 144D, mature wood; 200D.

*Stem size.*—Up to 1.5 m in length and 6 mm in diameter.

*Stem surface.*—Smooth.

*Stem aspect.*—Uniquely horizontal branching habit.

*Stem strength.*—Moderate to strong.

*Branching.*—Basal branching, an average of 20 lateral branches.

Foliage description:

*Leaf shape.*—Elliptical.

*Leaf division.*—Single.

*Leaf base.*—Rounded.

*Leaf apex.*—Broadly acute.

*Leaf fragrance.*—None.

*Leaf venation.*—Reticulate, color of upper and lower surfaces; mid rib 142C in color and conspicuous.

*Leaf margins.*—Entire.

*Leaf arrangement.*—Primarily alternate.

*Leaf attachment.*—Petiolate.

*Leaf surface.*—Leathery leaf texture, upper surface; smooth, lower surface; smooth with light pubescence.

*Leaf internode length.*—An average of 5 cm.

*Leaf size.*—An average of 6 cm in length and 4 cm in width.

*Leaf quantity.*—An average of 30 per stem.

*Leaf color.*—Young upper surface; 149C, young lower surface; 150D, mature upper surface; 141B, mature lower surface; 141C.

*Petioles.*—About 1 cm in length and 3 mm in width, smooth surface, color; 138B.

*Stipules.*—None.

Flower description:

*Inflorescence type.*—Single flowers from lateral stems.

*Flower number.*—Profuse, average of 10 to 20 per lateral stem, about 800 are produced on a plant six years in age.

*Flower fragrance.*—Light scent.

*Flower longevity.*—About 5 days.

*Flower type.*—Rotate, cupped when opening and becoming more horizontal.

*Flower aspect.*—Primarily upright to stem.

*Flower size.*—Average of 8 cm in diameter and 3 cm in depth.

*Peduncles.*—Medium strength, round in shape, average of 2 cm in length and 0.5 cm in diameter, surface covered in short pubescence, 165A in color.

*Flower buds.*—Ovoid in shape, an average of 3.5 cm in length and 1.5 cm in width, color; 155B and surrounded by an indumentum (bud casing) that is fuzzy and 163A in color.

*Sepals.*—None.

*Tepals.*—An average of 6 to 7 per flower, un-fused, whorled and slightly overlapping, self-cleaning, elliptical in shape, upper and lower surfaces velvety and smooth, margin entire, rounded base, broadly rounded apex, average of 4 cm in length and 1.5 cm in width, color: opening flowers and fully open upper and lower surfaces; 155B, fading to 155A.

Reproductive organs:

*Gynoecium.*—1 Pistil, about 2.5 cm in length, stigma is ovoid in shape, 0.5 cm in length and 145C in color, ovary is 154D in color, style is 2 cm in length and 144B in color.

*Androcoecium.*—Approximately 50 stamens, anthers are linear in shape, 2 mm in length and 145C in color, pollen is moderate in quantity and 4C in color.

*Fruit and seed.*—Fruit; compressed globose in shape, about 4 mm in diameter, 199A in color, seed; average of 8 to 10 seeds per fruit.

It is claimed:

1. A new and distinct cultivar of *Michelia* plant named 'Free Spirit' as herein illustrated and described.

* * * * *